(12) United States Patent
Bell et al.

(10) Patent No.: US 11,514,813 B2
(45) Date of Patent: Nov. 29, 2022

(54) SMART FITNESS SYSTEM

(71) Applicant: INTERNATIONAL BUSINESS MACHINES CORPORATION, Armonk, NY (US)

(72) Inventors: Denise Bell, Austin, TX (US); Jana H. Jenkins, Raleigh, NC (US); Jeffrey A. Kusnitz, Campbell, CA (US); Adriana Morales, Travis County, TX (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 1091 days.

(21) Appl. No.: 16/152,527

(22) Filed: Oct. 5, 2018

(65) Prior Publication Data

US 2020/0111384 A1   Apr. 9, 2020

(51) Int. Cl.
| | |
|---|---|
| *G09B 19/00* | (2006.01) |
| *G09B 5/02* | (2006.01) |
| *A63B 24/00* | (2006.01) |
| *G08B 21/02* | (2006.01) |
| *A63B 21/072* | (2006.01) |

(52) U.S. Cl.
CPC ........ *G09B 19/003* (2013.01); *A63B 24/0006* (2013.01); *G08B 21/02* (2013.01); *G09B 5/02* (2013.01); *A63B 21/0724* (2013.01); *A63B 2024/0009* (2013.01); *A63B 2024/0015* (2013.01); *A63B 2225/50* (2013.01)

(58) Field of Classification Search
CPC .... G09B 19/003; G09B 5/02; A63B 24/0006; A63B 21/0724; A63B 2024/0009; A63B 2024/0015; A63B 2225/50; G08B 21/02
See application file for complete search history.

(56) References Cited

U.S. PATENT DOCUMENTS

| | | | | |
|---|---|---|---|---|
| 5,016,035 A | * | 5/1991 | Myles, Jr. | G03B 17/40 396/2 |
| 5,846,086 A | * | 12/1998 | Bizzi | A63B 71/0622 482/902 |
| 6,783,247 B2 | * | 8/2004 | White | G03B 15/10 353/77 |

(Continued)

FOREIGN PATENT DOCUMENTS

| | | |
|---|---|---|
| CN | 201444959 U | 5/2010 |
| DE | 102012020314 B4 | 3/2015 |

(Continued)

*Primary Examiner* — Xuan M Thai
*Assistant Examiner* — Sadaruz Zaman
(74) *Attorney, Agent, or Firm* — Cantor Colburn LLP; Teddi Maranzano

(57) ABSTRACT

Methods, systems, and computer program products for analysis of movement patterns and corrective actions are provided. Aspects include capturing, via a camera, movement data associated with a user, analyzing the movement data to identify a movement pattern of the user, accessing, from a database, a model movement pattern for the movement pattern of the user, comparing the model movement pattern to the movement pattern of the user, determining a fault in the movement pattern of the user, and displaying, via a display screen, video data comprising a corrected movement pattern for the user based at least on the fault in the movement pattern of the user.

20 Claims, 6 Drawing Sheets

(56) References Cited

U.S. PATENT DOCUMENTS

| | | | | |
|---|---|---|---|---|
| 7,758,470 | B2 * | 7/2010 | Hirata | A63B 21/00181 |
| | | | | 482/901 |
| 9,088,787 | B1 * | 7/2015 | Smith | H04N 13/194 |
| 9,685,060 | B2 * | 6/2017 | Mantsvetov | G08B 21/02 |
| 10,758,780 | B2 * | 9/2020 | Putnam | H04N 21/4415 |
| 11,167,172 | B1 * | 11/2021 | Putnam | A63B 71/0622 |
| 2004/0219498 | A1 * | 11/2004 | Davidson | A63B 69/00 |
| | | | | 434/247 |
| 2010/0173276 | A1 * | 7/2010 | Vasin | A63B 69/004 |
| | | | | 434/323 |
| 2012/0079555 | A1 * | 3/2012 | Choi | G09B 19/0015 |
| | | | | 725/139 |
| 2012/0206577 | A1 * | 8/2012 | Guckenberger | G09B 19/003 |
| | | | | 348/47 |
| 2013/0004016 | A1 * | 1/2013 | Karakotsios | G06V 40/28 |
| | | | | 382/103 |
| 2015/0037771 | A1 * | 2/2015 | Kaleal, III | G16H 50/30 |
| | | | | 434/257 |
| 2015/0098143 | A1 * | 4/2015 | Anderson | G03B 21/62 |
| | | | | 359/839 |
| 2015/0099252 | A1 * | 4/2015 | Anderson | G06T 7/251 |
| | | | | 434/257 |
| 2016/0111017 | A1 * | 4/2016 | Chan | G02B 5/08 |
| | | | | 434/262 |
| 2016/0012279 | A1 | 10/2016 | Bludau et al. | |
| 2017/0076619 | A1 * | 3/2017 | Wallach | G09B 19/0038 |
| 2018/0025664 | A1 * | 1/2018 | Clarke | G09B 15/00 |
| | | | | 434/257 |
| 2018/0247560 | A1 * | 8/2018 | Mackenzie | G06T 7/248 |
| 2018/0350148 | A1 * | 12/2018 | George | G06V 40/20 |
| 2019/0103033 | A1 * | 4/2019 | Lu Hill | G06V 40/23 |
| 2020/0111384 | A1 * | 4/2020 | Bell | G09B 5/02 |
| 2021/0128978 | A1 * | 5/2021 | Gilstrom | A63B 71/0619 |
| 2021/0342952 | A1 * | 11/2021 | Putnam | A63B 24/0006 |
| 2022/0054925 | A1 * | 2/2022 | Chiang | A63B 24/0006 |
| 2022/0093230 | A1 * | 3/2022 | Gupta | A63B 24/0062 |

FOREIGN PATENT DOCUMENTS

| | | |
|---|---|---|
| JP | 2016174633 A | 10/2016 |
| JP | 20160012279 A | 10/2016 |

* cited by examiner

SMART FITNESS SYSTEM

BACKGROUND

The present invention generally relates to fitness, and more specifically, to a smart fitness system.

At most gyms or with most activities that focus on the form of a person's movement, there is typically a set of mirrors that allow a person to view and confirm or adjust their movements to account for the proper form of the movement. However, unless the person has an expert to analyze the movements, the person has an improper form for the movement which can result in a potential injury.

SUMMARY

Embodiments of the present invention are directed to a computer-implemented method for analysis of movement patterns and corrective actions. A non-limiting example of the computer-implemented method includes capturing, via a camera, movement data associated with a user, analyzing the movement data to identify a movement pattern of the user, accessing, from a database, a model movement pattern for the movement pattern of the user, comparing the model movement pattern to the movement pattern of the user, determining a fault in the movement pattern of the user, and displaying, via a display screen, video data comprising a corrected movement pattern for the user based at least on the fault in the movement pattern of the user.

Embodiments of the present invention are directed to a system for analysis of movement patterns and corrective actions. A non-limiting example of the system includes a processor communicatively coupled to a memory, the processor configured to perform capturing, via a camera, movement data associated with a user, analyzing the movement data to identify a movement pattern of the user, accessing, from a database, a model movement pattern for the movement pattern of the user, comparing the model movement pattern to the movement pattern of the user, determining a fault in the movement pattern of the user, and displaying, via a display screen, video data comprising a corrected movement pattern for the user based at least on the fault in the movement pattern of the user.

Embodiments of the invention are directed to a computer program product for analysis of movement patterns and corrective actions, the computer program product comprising a computer readable storage medium having program instructions embodied therewith. The program instructions are executable by a processor to cause the processor to perform a method. A non-limiting example of the method includes capturing, via a camera, movement data associated with a user, analyzing the movement data to identify a movement pattern of the user, accessing, from a database, a model movement pattern for the movement pattern of the user, comparing the model movement pattern to the movement pattern of the user, determining a fault in the movement pattern of the user, and displaying, via a display screen, video data comprising a corrected movement pattern for the user based at least on the fault in the movement pattern of the user.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

Figure 1:
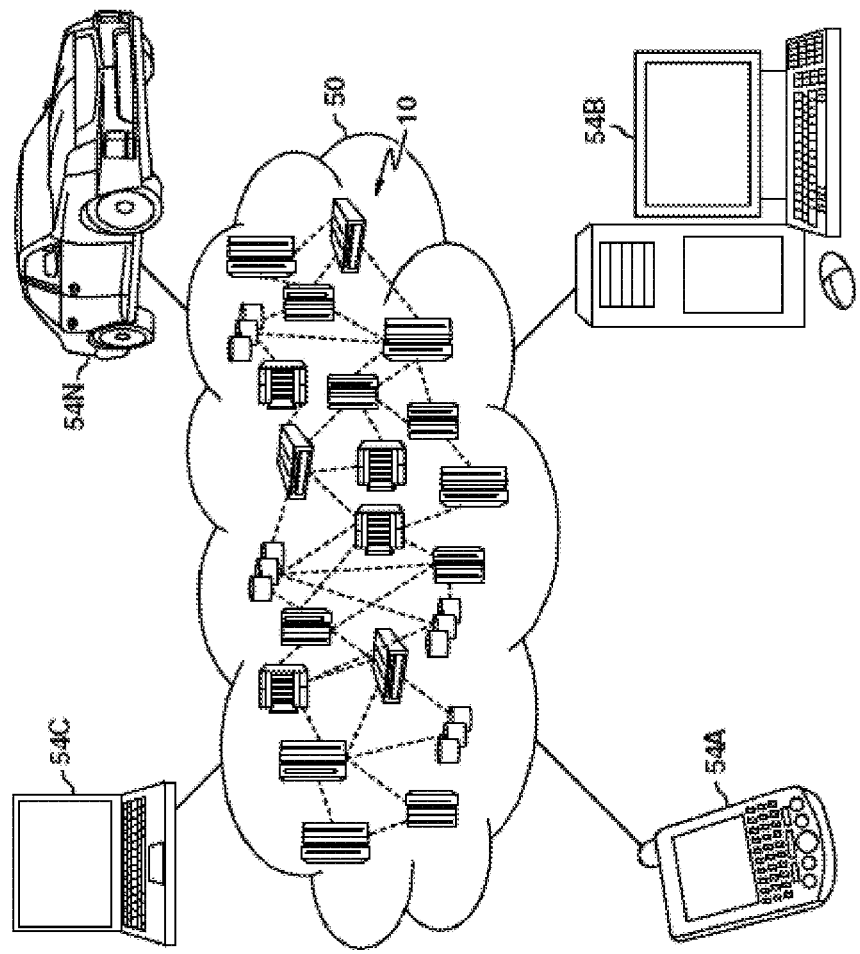
FIG. 1 depicts a cloud computing environment according to one or more embodiments of the present invention.

The diagrams depicted herein are illustrative. There can be many variations to the diagram or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the disclosed embodiments, the various elements illustrated in the figures are provided with two or three digit reference numbers. With minor exceptions, the leftmost digit(s) of each reference number correspond to the figure in which its element is first illustrated.

DETAILED DESCRIPTION

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising,"

"includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" may be understood to include any integer number greater than or equal to one, i.e. one, two, three, four, etc. The terms "a plurality" may be understood to include any integer number greater than or equal to two, i.e. two, three, four, five, etc. The term "connection" may include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 1, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
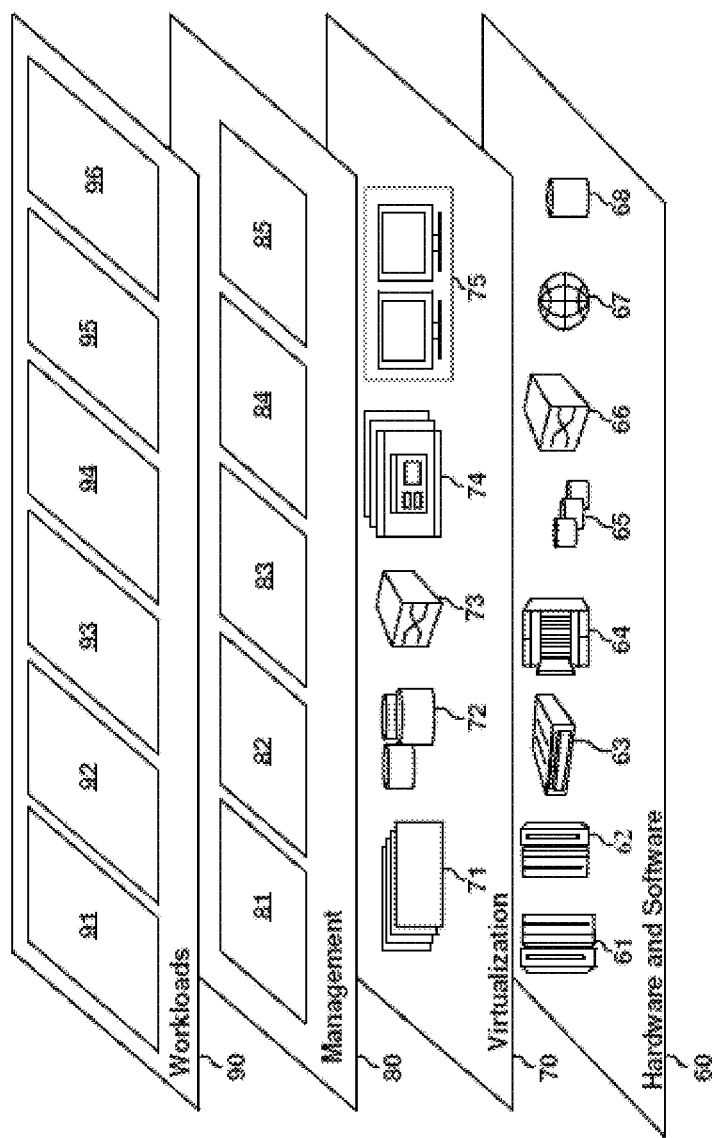
FIG. 2 depicts abstraction model layers according to one or more embodiments of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components.

Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provides pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and smart fitness coach 96.

Figure 3:
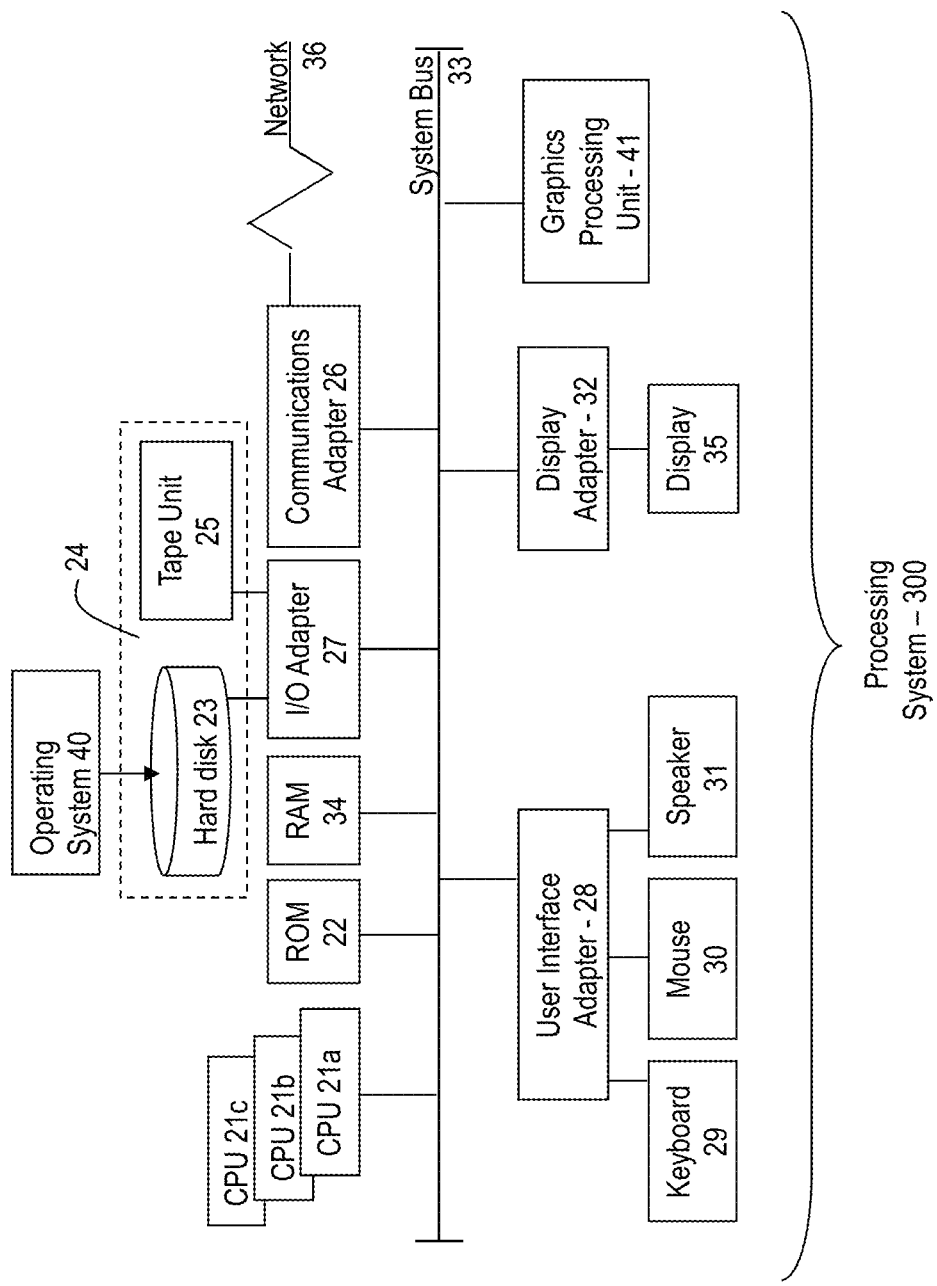
FIG. 3 depicts a block diagram of a computer system for use in implementing one or more embodiments of the present invention.

Referring to FIG. 3, there is shown an embodiment of a processing system 300 for implementing the teachings herein. In this embodiment, the system 300 has one or more central processing units (processors) 21a, 21b, 21c, etc. (collectively or generically referred to as processor(s) 21). In one or more embodiments, each processor 21 may include a reduced instruction set computer (RISC) microprocessor. Processors 21 are coupled to system memory 34 and various other components via a system bus 33. Read only memory (ROM) 22 is coupled to the system bus 33 and may include a basic input/output system (BIOS), which controls certain basic functions of system 300.

FIG. 3 further depicts an input/output (I/O) adapter 27 and a network adapter 26 coupled to the system bus 33. I/O adapter 27 may be a small computer system interface (SCSI) adapter that communicates with a hard disk 23 and/or tape storage drive 25 or any other similar component. I/O adapter 27, hard disk 23, and tape storage device 25 are collectively referred to herein as mass storage 24. Operating system 40 for execution on the processing system 300 may be stored in mass storage 24. A network adapter 26 interconnects bus 33 with an outside network 36 enabling data processing system 300 to communicate with other such systems. A screen (e.g., a display monitor) 35 is connected to system bus 33 by display adaptor 32, which may include a graphics adapter to improve the performance of graphics intensive applications and a video controller. In one embodiment, adapters 27, 26, and 32 may be connected to one or more I/O busses that are connected to system bus 33 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 33 via user interface adapter 28 and display adapter 32. A keyboard 29, mouse 30, and speaker 31 all interconnected to bus 33 via user interface adapter 28, which may include, for example, a Super I/O chip integrating multiple device adapters into a single integrated circuit.

In exemplary embodiments, the processing system 300 includes a graphics processing unit 41. Graphics processing unit 41 is a specialized electronic circuit designed to manipulate and alter memory to accelerate the creation of images in a frame buffer intended for output to a display. In general, graphics processing unit 41 is very efficient at manipulating computer graphics and image processing and has a highly parallel structure that makes it more effective than general-purpose CPUs for algorithms where processing of large blocks of data is done in parallel.

Thus, as configured in FIG. 3, the system 300 includes processing capability in the form of processors 21, storage capability including system memory 34 and mass storage 24, input means such as keyboard 29 and mouse 30, and output capability including speaker 31 and display 35. In one embodiment, a portion of system memory 34 and mass storage 24 collectively store an operating system coordinate the functions of the various components shown in FIG. 3.

Turning now to an overview of technologies that are more specifically relevant to aspects of the invention, proper form can be helpful when performing certain types of movements such as weight training exercises, cardiovascular exercises, yoga, dancing, and physical therapy. Improper form for these types of movement has the potential to lead to injury. A need exists for a user at a gym, dance studio, or similar workout environment to get feedback and correction on their physical movements.

Turning now to an overview of the aspects of the invention, one or more embodiments of the invention address the above-described shortcomings of the prior art by providing a system that utilizes two-way mirrors with a built-in motion tracking camera(s). When a user is in front of the system, the user turns on the mirrors and enters information, for example, height, weight, and workout type or program or dance etc. This information is used to calibrate the mirrors. The system has been previously trained by recording experts as they do the moves in correct form and speed. As the participant goes through their movements, the system provides feedback on any recommended corrections. This feedback can occur in real-time as well as in a recording. The movement that is not optimal yet will be highlighted and the correct position shown.

Figure 4:
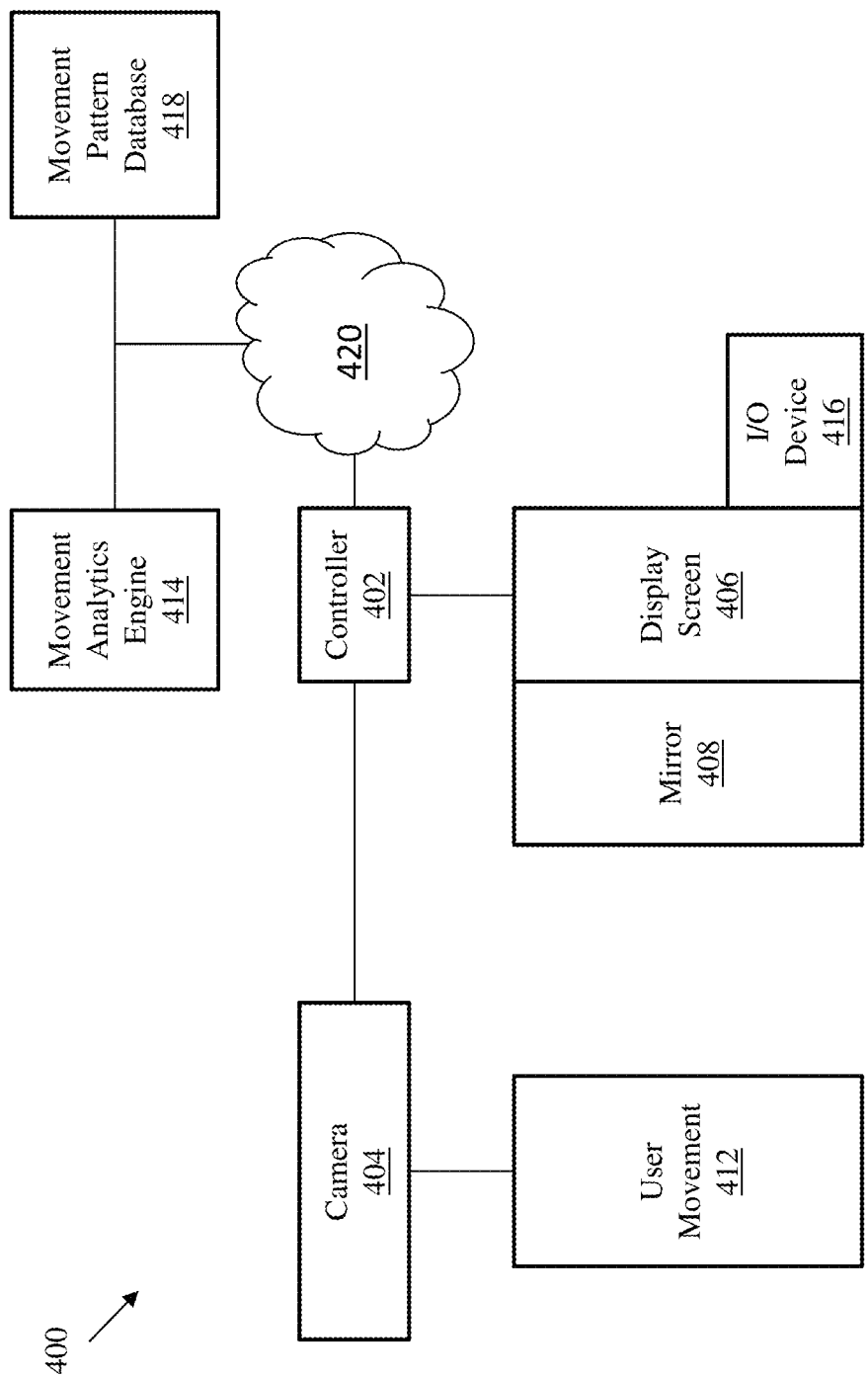
FIG. 4 depicts a system for analysis of movement patterns and corrective actions according to one or more embodiments of the invention.

Turning now to a more detailed description of aspects of the present invention, FIG. 4 depicts a block diagram of a system for analysis of movement patterns and corrective actions according to embodiments of the invention. The system 400 includes a display screen 406, a mirror, and a camera 404. In embodiments of the invention, the mirror 408 can be a two-way mirror with the display screen 406 arranged behind the mirror 408 such that the display screen 406 output is visible through the mirror 408. The camera 404 is operable to capture one or more images or video of a user using the system 400. Particularly, the camera 404 can capture the user movement 412 for analysis. The system also includes a controller 402 that can operate the camera 404 and the display screen 406. The controller 402 can include a transceiver that can transmit and receive data through a network 420. The system also includes a movement analytics engine 414 that can be located on a cloud server or located locally to the system 400. The camera 404 can provide the image or video data capturing the user movement 412 to the controller 402 which can share the image or video data with the movement analytics engine 414 either directly (if local to the controller) or through the network 420 (if on a cloud server). The movement analytics engine 414 can analyze the user movement 412, utilizing pattern recognition, image recognition, and any other machine learning algorithms, to determine what type of movement the user is attempting to perform. For example, a user may wish to check if his or her form when performing a squat is correct or not. The user performs the exercise in front of the mirror 408 and the camera 404 captures the user movement 412. The controller 402 transmits this image or video data from the camera 404 to the movement analytics engine 414 to determine the type of exercise being performed. The movement analytics engine 414 can then obtain a model movement pattern (e.g., video or image data of an expert performing a squat) for comparison from a movement pattern database 418. Using a machine learning model, the movement analytics engine 414 can compare the user movement 412 to the model movement pattern to determine a level of difference between the two. In one or more embodiments, a comparison score can be obtained based on the differences between the user movement 412 images and the model movement pattern images. This may be performed by comparing pixel values the user movement 412 images and the model movement pattern images, or by any other known image comparison tool. A difference in pixel value for the user movement 412 and the model movement pattern image can indicate a change between these images. The absolute values of all the pixel differences between the new image and the reference image may then be summed to generate a comparison score. The pixel comparisons may be made, for example, based on a change in color, change in brightness, etc. Comparing pixel values is merely exemplary and not intended to limit the application, uses, and/or technical scope for image or video analytics, which can be embodied utilizing various techniques. The pixel comparison is a non-limiting example presented for illustrative and explanatory purposes.

In embodiments of the invention, the engines 402 can also be implemented as so-called classifiers (described in more detail below). In one or more embodiments of the invention, the features of the various engines/classifiers (402) described herein can be implemented on the processing system 300 shown in FIG. 3, or can be implemented on a neural network (not shown). In embodiments of the invention, the features of the engines/classifiers 402 can be implemented by configuring and arranging the processing system 300 to execute machine learning (ML) algorithms. In general, ML algorithms, in effect, extract features from received data (e.g., inputs to the engines 402) in order to "classify" the received data. Examples of suitable classifiers include but are not limited to neural networks (described in greater detail below), support vector machines (SVMs), logistic regression, decision trees, hidden Markov Models (HMMs), etc. The end result of the classifier's operations, i.e., the "classification," is to predict a class for the data. The ML algorithms apply machine learning techniques to the received data in order to, over time, create/train/update a unique "model." The learning or training performed by the engines/classifiers 402 can be supervised, unsupervised, or a hybrid that includes aspects of supervised and unsupervised learning. Supervised learning is when training data is already available and classified/labeled. Unsupervised learning is when training data is not classified/labeled so must be developed through iterations of the classifier. Unsupervised learning can utilize additional learning/training methods including, for example, clustering, anomaly detection, neural networks, deep learning, and the like.

In one or more embodiments of the invention, once the movement analytics engine 414 performs the comparison of the user movement 412 and the model movement pattern, the movement analytics engine 414 can determine a fault in the user movement 412. The fault can indicate an improper or unsafe movement pattern (e.g., the user is relying on his or her back to lift weight). The movement analytics engine 414 can generate a corrective movement pattern using the model movement pattern and display the corrective movement pattern to the user on the display screen 406. The user can view the corrective movement pattern on the display screen 406 responsive to receiving a notification that their user movement 412 is incorrect or unsafe. For example, while performing an exercise in front of the mirror 408, an icon or an alert can be displayed on the display screen 406 to draw the attention of the user. The can acknowledge the alert using an input/output device 416, such as a keypad or other input means. Responsive to the user acknowledging the alert, the movement analytics engine 414 can utilize the controller 402 to display the corrected movement pattern on the display screen 406. In embodiments of the invention, the user can indicate through the I/O device 416 before starting his or her exercise whether they want their exercise to be analyzed and receive feedback from the system 400.

In one or more embodiments, the mirror 408 is optional for the system 400. The camera 404 can capture the user movement 412 in real time and display the real-time user movement 412 on the display screen 406 emulating the mirror 408 functionality (i.e., reversing the video of the user movement 412 to simulate how a mirror would reflect the user movement 412). In one or more embodiments, the camera 404 can be any type of camera that can be used to generate video and/or still frame images. The cameras can capture any type of video images such as, for example, infrared images, depth, image, and the like. The cameras mentioned herein are only examples of suitable camera types and are not intended to suggest any limitation as to the scope of use or functionality of the cameras. In embodiments, the movement analytics engine 414 can transmit a request for an adjustment to the camera 404 by the controller 402 to better capture the user movement 412. This request can include an adjustment to the position, zoom, orientation, and the like, of the camera. The camera, itself, can be adjustable to pan, zoom, and focus on multiple aspects of the user movement 412.

Figure 5:
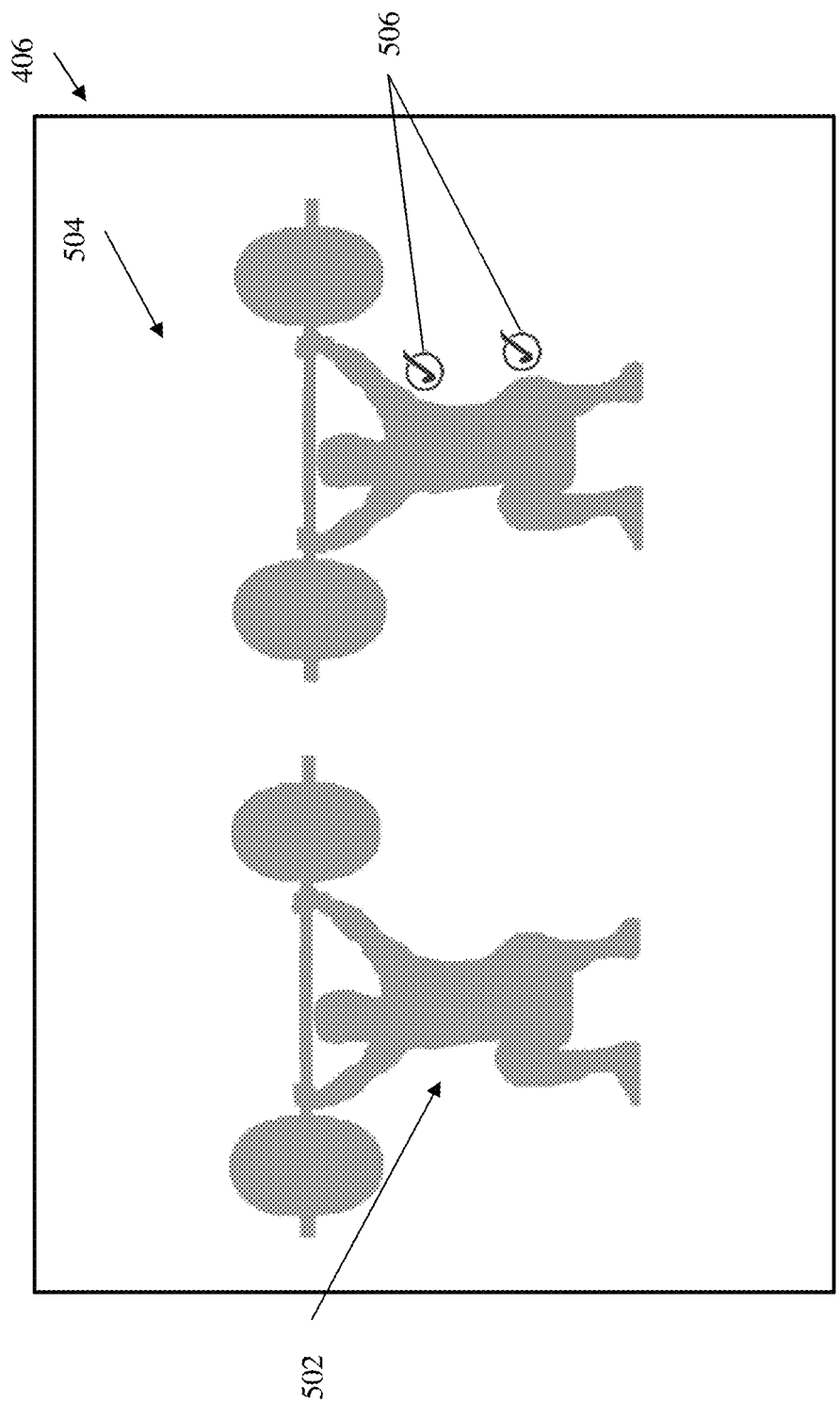
FIG. 5 depicts an exemplary display screen image for a user movement according to one or more embodiments of the invention.

In one or more embodiments of the invention, the display screen 406 can display both corrective movement patterns as well as positive feedback on the user movement 412 to the user. For example, the system 400 can confirm that a user is performing a movement correctly. FIG. 5 depicts an exemplary display screen 406 image for a user movement according to one or more embodiments of the invention. The display screen 406 includes an image/video 502 of the user performing a movement. In embodiments, the display screen 406 can display a feedback image/video 504 with icons 506 overlaid on the feedback image/video 504 indicating either a correct or incorrect movement by the user. While the illustrative example shows a correct movement being displayed, any feedback for the user movement can be provided including negative feedback indicating that the user is performing the movement incorrectly. The images or video displayed on the display screen 406 can provide instruction on how to correct the user's movement or can simply display the model movement pattern to the user for reference.

In one or more embodiments, the system 400 can receive information about the user before analyzing the user movement 412. The user can input into the I/O device 416 information such as height, weight, sex, and any other information related to the user's workout routine, such as exercise type, and the like. The movement analytics engine 414 can utilize this information about the user to build a user profile for the user and further utilize this information when selecting a model movement pattern to compare to the user movement 412. For example, the body type and age of the user may limit the range of motion of the user such that the comparison to a model movement pattern would need more relaxed standards for comparison. The user profile for the user can store historical exercise data (e.g., image and video) of the user. In embodiments, the movement analytics engine 414 can identify and track the progress of a user through a workout routine (e.g., flexibility, range of motion, etc.). The progress of the user can be shared with another user such as a trainer or therapist. In embodiments, the system 400 can be utilized with physical therapy for a patient. The system 400 can track a patient's progress through a therapy treatment, for example. The system 400 can alert a therapist when certain metrics have been met such as an increase in the range of motion, strength, flexibility, and the like. In embodiments, the system 400 can identify unsafe conditions in a user movement 412 such as poor form or posture which can result in injury to the user. Based on the unsafe condition, the system 400 can generate an alert for display on the display screen 406 or can transmit an alert to a trainer, therapist, or other user to intervene.

In one or more embodiments of the invention, the system 400 can be deployed in a non-exercise setting. For example, the system 400 can be utilized in an office setting for an individual wishing to correct their posture while at their desk. The camera 404 can capture the user's posture and compare it to model posture. The system 400 can alert the user, either through their computer display screen or to their smart device, that their posture is improper and suggest adjusting their posture while at their desk, for example.

In one or more embodiments of the invention, the cloud computing system 50 can be in wired or wireless electronic communication with one or all of the elements of the system 400. Cloud 50 can supplement, support or replace some or all of the functionality of the elements of the system 400. Additionally, some or all of the functionality of the elements of system 400 can be implemented as a node 10 (shown in FIGS. 1 and 2) of cloud 50. Cloud computing node 10 is only one example of a suitable cloud computing node and is not intended to suggest any limitation as to the scope of use or functionality of embodiments of the invention described herein.

Figure 6:
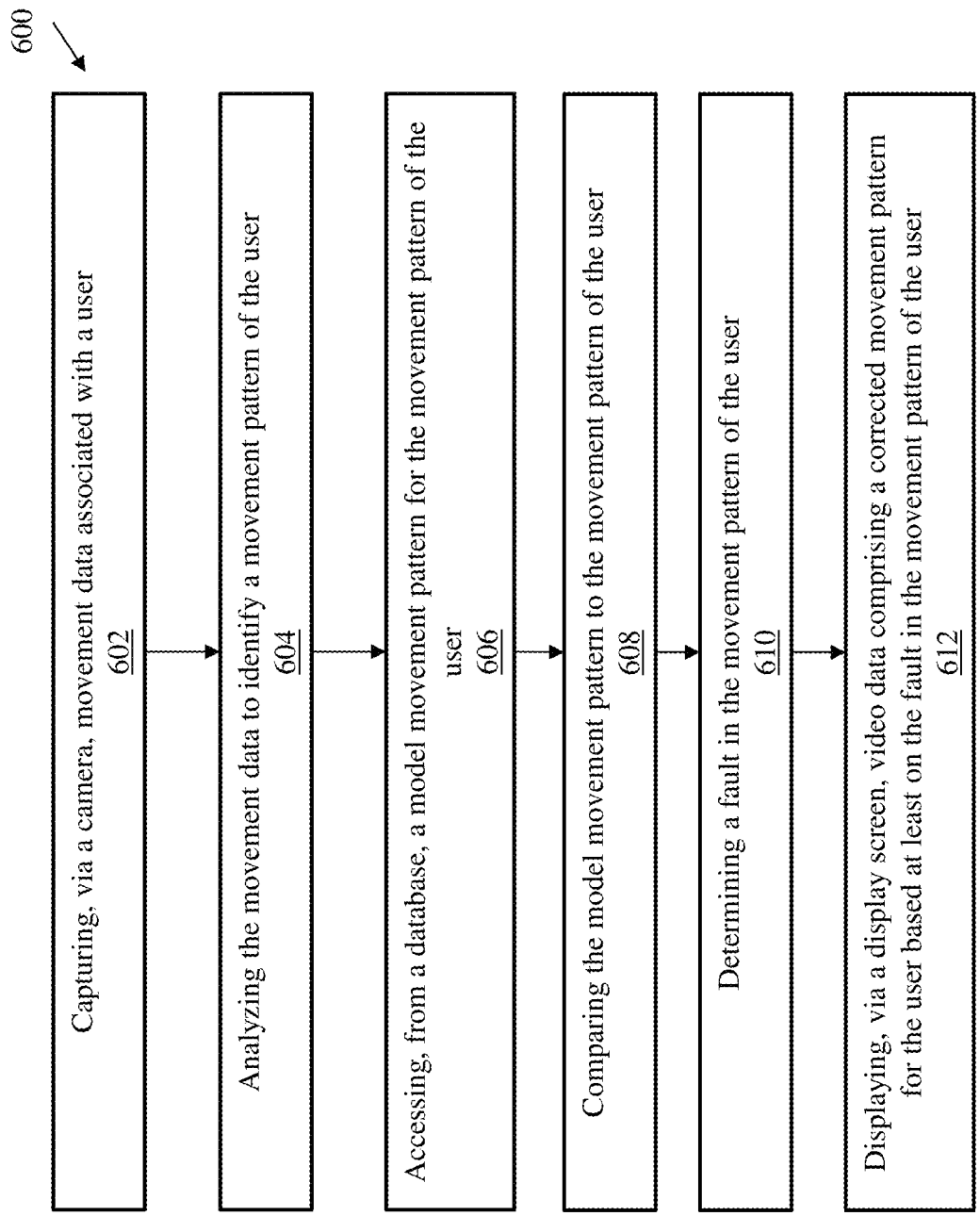
FIG. 6 depicts a flow diagram of a method for analysis of movement patterns and corrective actions according to one or more embodiments of the invention.

FIG. 6 depicts a flow diagram of a method for analysis of movement patterns and corrective actions according to one or more embodiments of the invention. The method 600 includes capturing, via a camera, movement data associated with a user, as shown in block 602. Once the movement data is captured, the method 600 includes analyzing the movement data to identify a movement pattern of the user, as shown in block 604. The movement pattern can be any of an exercise type, dance type, or therapeutic movement. At block 606, the method 600 includes accessing, from a database, a model movement pattern for the movement pattern of the user. The model movement pattern can be selected based on the user information such as age, height, etc. Then at block 608, the method 600 includes comparing the model movement pattern to the movement pattern of the user. The method 600, at block 610, includes determining a fault in the movement pattern of the user. And at block 612, the method 600 includes displaying, via a display screen, video data comprising a corrected movement pattern for the user based at least on the fault in the movement pattern of the user. In one or more embodiments, the method 600 can determine positive feedback for the movement pattern to indicate that the user is performing the movement correctly and display the positive feedback to the user on the display screen.

Additional processes may also be included. It should be understood that the processes depicted in FIG. 6 represent illustrations, and that other processes may be added or existing processes may be removed, modified, or rearranged without departing from the scope and spirit of the present disclosure.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer-implemented method for analysis of movement patterns and corrective actions, the method comprising:
   capturing, via a camera, movement data associated with a user performing a movement pattern;
   analyzing the movement data to identify the movement pattern of the user;
   accessing, from a database, a model movement pattern for the movement pattern of the user;
   comparing the model movement pattern to the movement pattern of the user;
   based on determining a fault in the movement pattern of the user, displaying, via a display screen arranged behind a two-way mirror, an alert to the user indicating that the movement pattern of the user is improper; and
   responsive to the user acknowledging the alert, displaying, via the display screen arranged behind the two-way mirror, video data comprising a corrected movement pattern for the user, wherein the corrected movement pattern includes an indication of the fault in the movement pattern of the user.

2. The computer-implemented method of claim 1, wherein capturing the movement data associated with the user is responsive to a detection, by the camera, of a presence of the user within a predefined range of the display screen.

3. The computer-implemented method of claim 1, further comprising building a user profile comprising one or more characteristics of the user, wherein the model movement pattern is accessed based at least in part on the one or more characteristics of the user.

4. The computer-implemented method of claim 3, wherein the one or more characteristics of the user comprise height of the user, weight of the user, and age of the user.

5. The computer-implemented method of claim 3, wherein the one or more characteristics are inputted by the user.

6. The computer-implemented method of claim 3, wherein the one or more characteristics are determined from the movement data of the user.

7. The computer-implemented method of claim 1, further comprises:
obtaining historical movement data of the user;
comparing the movement pattern of the user to the historical movement data of the user to identify an improvement to the movement pattern of the user; and
storing the improvement to the movement pattern of the user in a memory.

8. The computer-implemented method of claim 1, wherein the movement data comprises video of the user performing a physical movement.

9. The computer-implemented method of claim 1, wherein the movement data comprises one or more images of the user performing a physical movement.

10. The computer-implemented method of claim 1, wherein the determining the fault in the movement pattern of the user comprises:
extracting, by a machine learning model, a first plurality of features from the movement pattern of the user to generate a first feature vector;
extracting, by the machine learning model, a second plurality of features from the model movement pattern to generate a second feature vector;
comparing the first feature vector to the second feature vector to determine a difference score, wherein the fault is determined based on the difference score exceeding a threshold difference score.

11. The computer-implemented method of claim 1, further comprising:
operating the camera to adjust at least one characteristic of the camera to capture one or more images of the movement pattern of the user.

12. The computer-implemented method of claim 11, wherein the at least one characteristic comprises a pan, a tilt, and a zoom for the camera.

13. The computer-implemented method of claim 1, further comprising:
analyzing the movement pattern of the user to identify a hazardous condition; and
transmitting an alert based on the hazardous condition.

14. The computer-implemented method of claim 1, wherein the movement pattern comprises an exercise performed by the user.

15. The computer-implemented method of claim 1, wherein the display screen is arranged behind a mirror.

16. A system for analysis of movement patterns and corrective actions, the system comprising:
a processor communicative coupled to a memory, the processor configured to:
capture, via a camera, movement data associated with a user performing a movement pattern;
analyze the movement data to identify the movement pattern of the user;
access, from a database, a model movement pattern for the movement pattern of the user;
compare the model movement pattern to the movement pattern of the user;
based on a determination that a fault exists in the movement pattern of the user, display, via a display screen arranged behind a two-way mirror, an alert to the user indicating that the movement pattern of the user is improper; and
responsive to the user acknowledging the alert, display, via the display screen arranged behind the two-way mirror, video data comprising a corrected movement pattern for the user, wherein the corrected movement pattern includes an indication of the fault in the movement pattern of the user.

17. The system of claim 16, wherein the determining the fault in the movement pattern of the user comprises:
extracting, by a machine learning model, a first plurality of features from the movement pattern of the user to generate a first feature vector;
extracting, by the machine learning model, a second plurality of features from the model movement pattern to generate a second feature vector;
comparing the first feature vector to the second feature vector to determine a difference score, wherein the fault is determined based on the difference score exceeding a threshold difference score.

18. A computer program product for analysis of movement patterns and corrective actions, the computer program product comprising a computer readable storage medium having program instructions embodied therewith, wherein the computer readable storage medium is not a transitory signal per se, the program instructions executable by a processor to cause the processor to perform a method comprising:
capturing, via a camera, movement data associated with a user performing a movement pattern;
analyzing the movement data to identify the movement pattern of the user;
accessing, from a database, a model movement pattern for the movement pattern of the user;
comparing the model movement pattern to the movement pattern of the user;
based on determining a fault in the movement pattern of the user, displaying, via a display screen arranged behind a two-way mirror, an alert to the user indicating that the movement pattern of the user is improper; and
responsive to the user acknowledging the alert, displaying, via the display screen arranged behind the two-way mirror, video data comprising a corrected movement pattern for the user, wherein the corrected movement pattern includes an indication of the fault in the movement pattern of the user.

19. The computer program product of claim 18, further comprises:
obtaining historical movement data of the user;
comparing the movement pattern of the user to the historical movement data of the user to identify an improvement to the movement pattern of the user; and
storing the improvement to the movement pattern of the user in a memory.

20. The computer program product of claim 18, wherein the determining the fault in the movement pattern of the user comprises:
extracting, by a machine learning model, a first plurality of features from the movement pattern of the user to generate a first feature vector;

extracting, by the machine learning model, a second plurality of features from the model movement pattern to generate a second feature vector;

comparing the first feature vector to the second feature vector to determine a difference score, wherein the fault is determined based on the difference score exceeding a threshold difference score.

\* \* \* \* \*